United States Patent [19]

Mrava et al.

[11] 4,149,538
[45] Apr. 17, 1979

[54] RESECTOSCOPE ELECTRODE ASSEMBLY WITH NON-CONDUCTIVE BEARING TUBE AND METHOD OF MAKING THE SAME

[75] Inventors: Gene L. Mrava, Wheeling; William P. McVay, Mundelein, both of Ill.

[73] Assignee: American Hospital Supply Corporation, Evanston, Ill.

[21] Appl. No.: 824,839

[22] Filed: Aug. 15, 1977

[51] Int. Cl.² .............................................. A61B 17/32
[52] U.S. Cl. ...................................................... 303.15
[58] Field of Search ........................ 128/303.13–303.17

[56] References Cited

U.S. PATENT DOCUMENTS

| | | | |
|---|---|---|---|
| 2,448,741 | 9/1948 | Scott et al. | 128/308.15 |
| 2,888,017 | 5/1959 | Wallace | 128/303.15 |
| 3,752,159 | 8/1973 | Wappler | 128/303.15 |
| 3,856,015 | 12/1974 | Iglesias | 128/303.15 |
| 3,901,242 | 8/1975 | Storz | 128/303.15 |
| 3,939,839 | 2/1976 | Curtiss | 128/303.15 |
| 3,973,568 | 8/1976 | Iglesias | 128/303.15 |

*Primary Examiner*—Lee S. Cohen
*Attorney, Agent, or Firm*—Tilton, Fallon, Lungmus & Chestnut

[57] ABSTRACT

A resectoscope electrode assembly having a non-cylindrical bearing tube formed of electrically non-conductive plastic material for slidable mounting upon the endoscope stem of a resectoscope. An electrode extends through a separate passage in the same bearing tube and is in direct electrical contact with that tube. One section of the electrode takes the form of a pair of spaced parallel arms projecting forwardly from the front end of the tube and terminating in an electrode tip, commonly in the form of an arcuate cutting loop. Another section of the electrode comprises a lead which extends from the rear end of the tube and which terminates in an offset connecting portion for engagement with and retention by the connector of the resectoscope. The lead and arms are encased in insulating sleeves, such sleeves being buried in and sealed to the bearing tube to prevent arcing between the bare electrode within that tube and the metal endoscope upon which the bearing tube is slidably supported. The method of making the assembly and the instrument with which that assembly is operatively associated are also disclosed.

19 Claims, 8 Drawing Figures

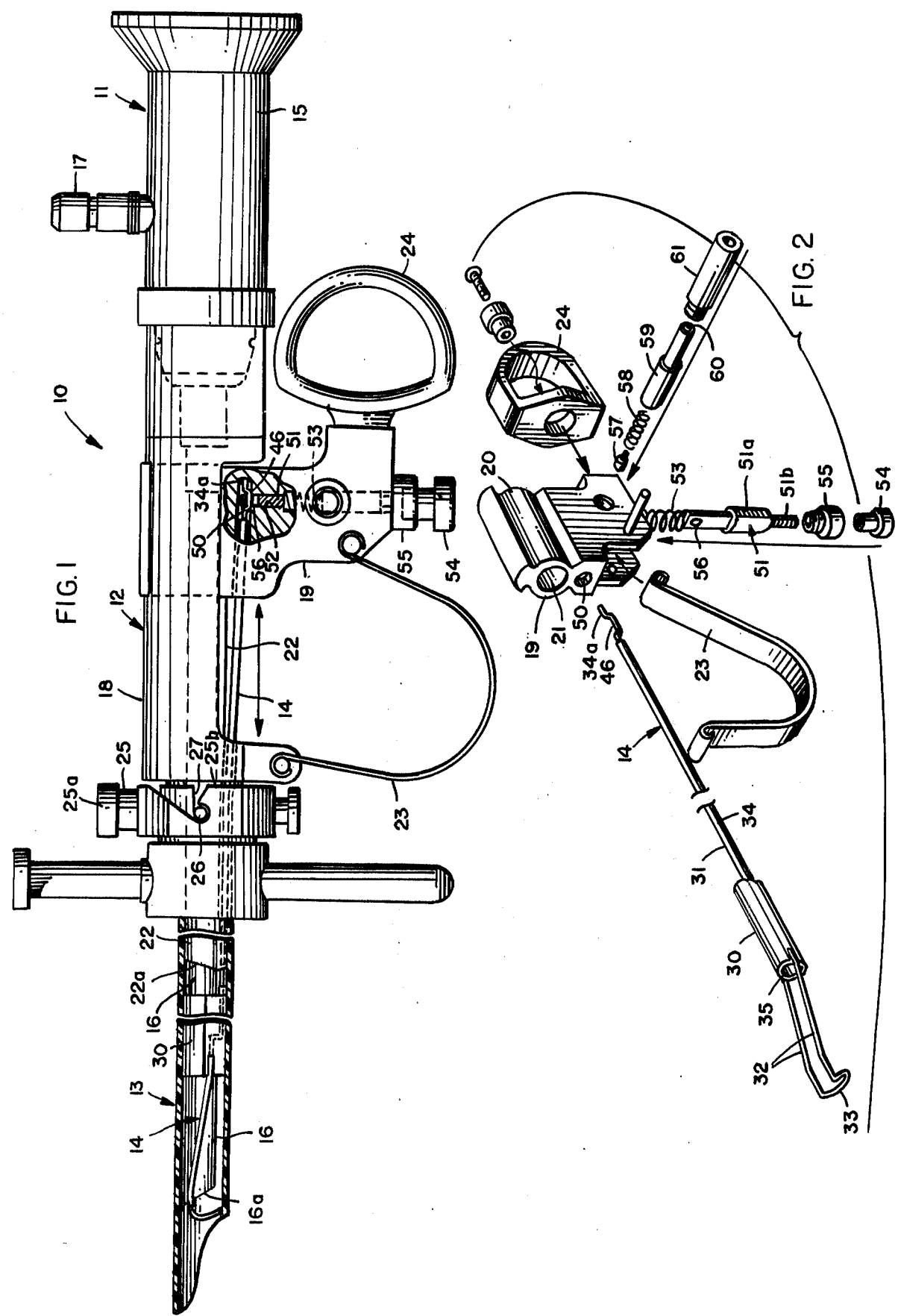

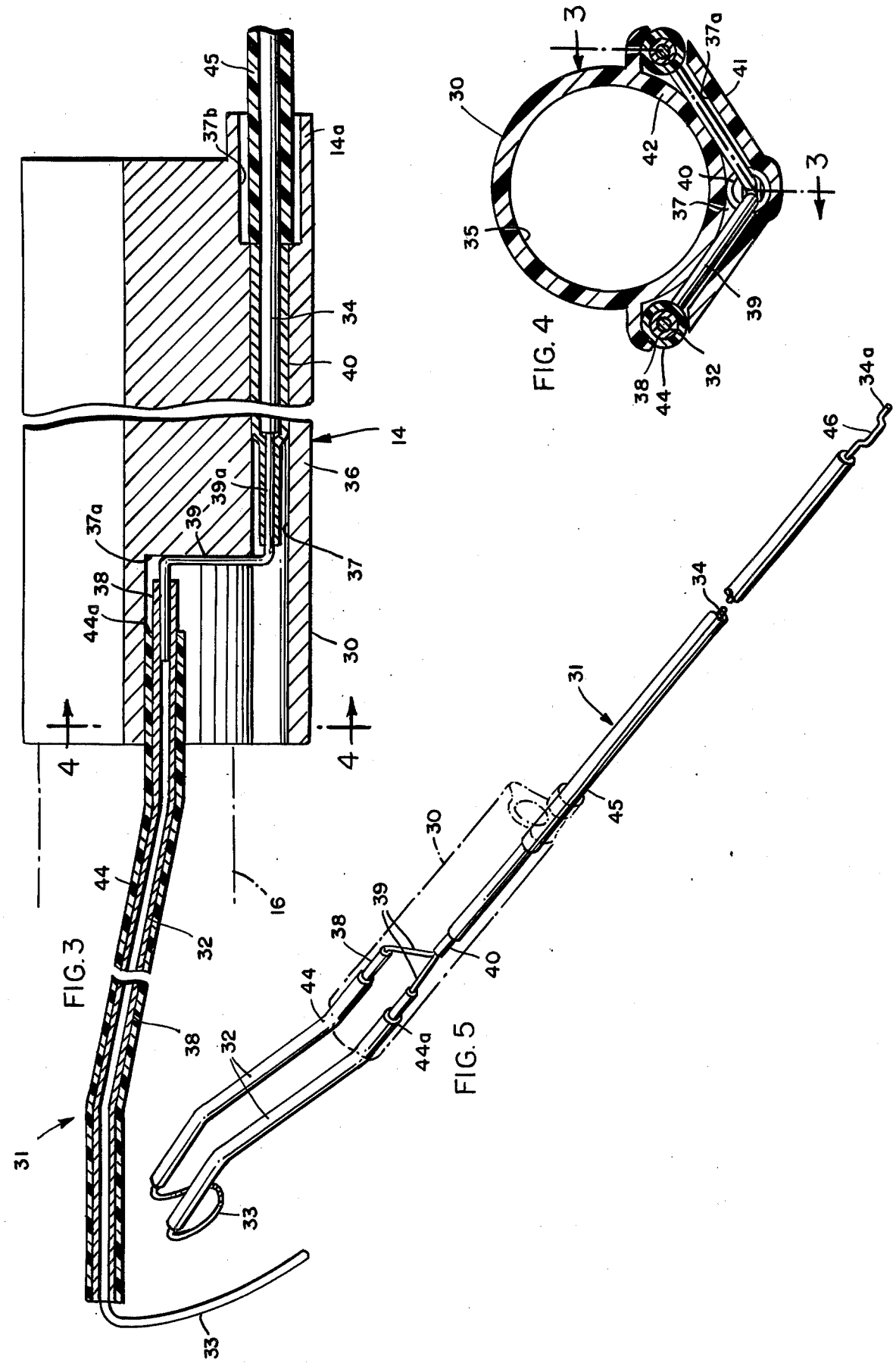

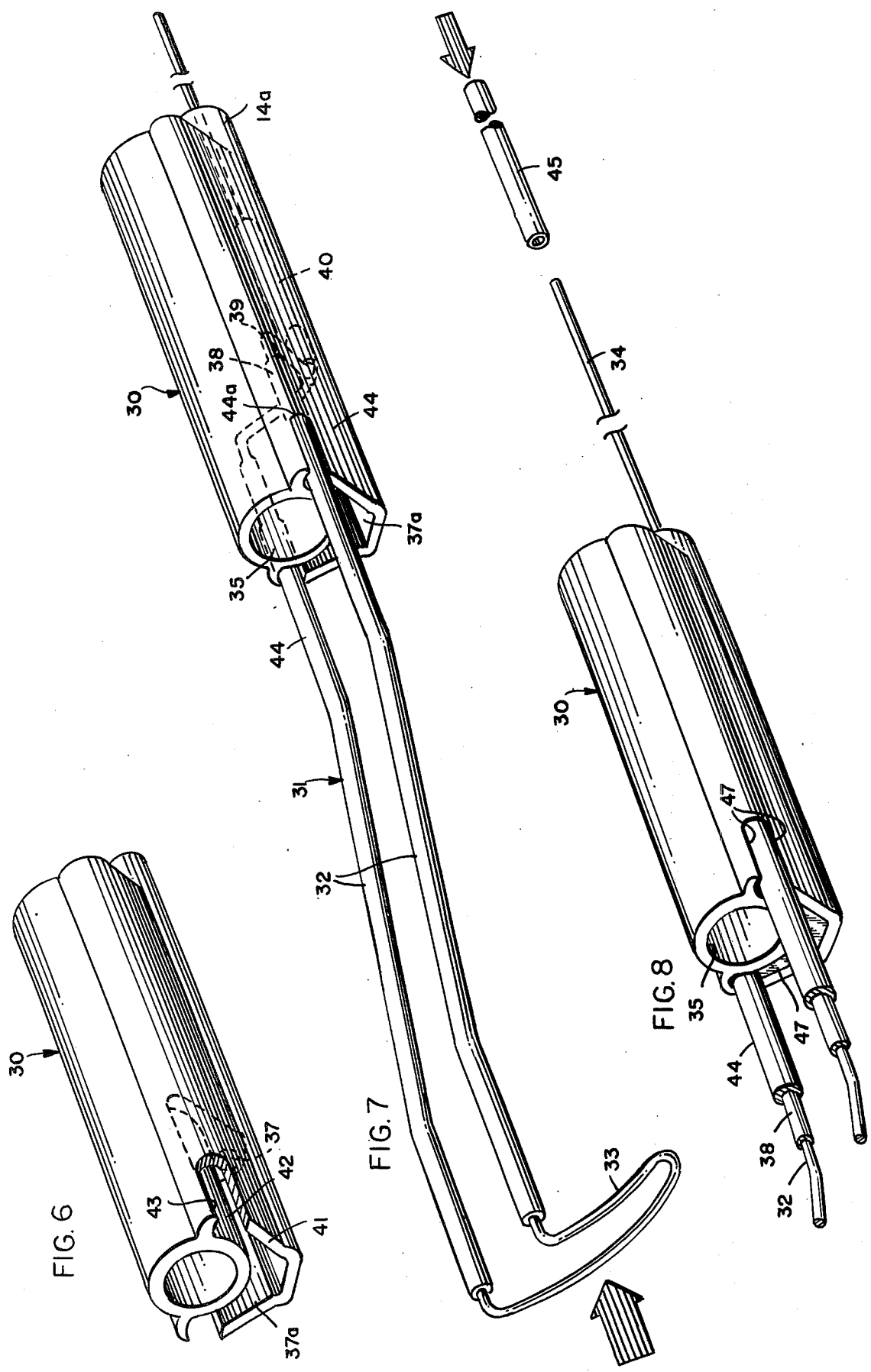

RESECTOSCOPE ELECTRODE ASSEMBLY WITH NON-CONDUCTIVE BEARING TUBE AND METHOD OF MAKING THE SAME

BACKGROUND

A typical resectoscope for transurethral resection consists of four main elements. The first element is a rigid endoscope or telescope for observing the interior of the human bladder, or operative sites near the base of the urethra. The endoscope comprises an objective lens and a series of relay lenses housed within an endoscope barrel or stem, the stem being connected to an eyepiece housing containing suitable lenses for proper magnification. The second element takes the form of a handle assembly commonly referred to as a working element. The working element serves as the means for connecting electrosurgical current from an electrosurgical generator to the third element, an electrode assembly. The working element is also capable of slidably moving the electrode assembly axially, such axial movement being observable through the eyepiece of the endoscope. The combination of the endoscope, working element, and electrode assembly is locked into a fourth element, a resectoscope sheath. The sheath consists of a non-conductive tube and a union body and lock assembly. In an operative procedure the sheath is placed into the urethra prior to introduction of the other elements.

The usual resectoscope electrode assembly takes the form of a U-shaped tungsten wire loop, the ends of the loop being joined to a pair of spaced parallel wire arms which extend along, but are spaced from, the distal end of the rigid endoscope. The wire arms usually merge at their proximal ends and are joined to an electrode lead extending back to the working element of the instrument. To brace the cutting loop so that it remains uniformly spaced from the endoscope stem, a spacing sleeve is commonly provided between the stem and either the parallel electrode arms or the distal portion of the electrode lead immediately adjacent those arms. The metal sleeve is slidable along the endoscope stem as the electrode assembly is advanced and retracted and, because of the direct contact between the sleeve and stem, it has been necessary in the past to insulate the electrode from the sleeve. Reference is made to U.S. Pat. Nos. 3,856,015, 3,901,242, 2,752,159, and 2,448,741 to illustrate prior cutting electrode assemblies.

The material and assembly costs of prior electrode assemblies has tended to encourage repeated use of such assemblies in contrast to replacement after each operative procedure. Reuse, even to a limited extent, presents risks for patients and doctors because the tungsten wire of the electrodes tends to become brittle, deformed, oxidized, and weakened even after only a single use. Should a worn electrode element break or fragment during a subsequent use, or should it become so weakened that it bends into arcing contact with the metal endoscope stem, then the possibilities of injury to either the patient or the doctor, or both, could be substantial. The problem is particularly serious because it may be difficult if not impossible to determine from the examination of a used electrode assembly that the tip or cutting element of that assembly has been damaged or weakened.

SUMMARY

This invention is concerned with a disposable electrode assembly; that is, an assembly which is not only highly effective but is sufficiently inexpensive in construction that it is economically feasible to discard each such assembly after a single operative procedure. Despite its relatively low cost, the new electrode assembly is superior to earlier construction in terms of mechanical and electrical performance.

Unlike earlier constructions, the electrode assembly of this invention utilizes an insulating or non-conductive plastic bearing tube for slidably engaging the rigid endoscope stem of the instrument. Although the dielectric tube is formed of a rigid plastic, its hardness is nevertheless substantially lower than that of the metal stem (ordinarily stainless steel) of the endoscope. The result is a smooth, non-abrading, and virtually noiseless sliding relationship between the bearing tube and the endoscope stem.

The plastic bearing tube serves as its own electrical insulator, thereby eliminating the need for separate insulation between electrode and the bearing tube. The fact that the electrode is in direct electrical contact with the bering tube is of no consequence because of the insulaing properties of the tube itself and because of the configuration and bulk of the tube which enhance the insulating effectiveness.

In brief, the electrode assembly comprises a bearing tube of non-cylindrical configuration having a wall defining an axial bore for slidably receiving the endoscope stem. The tube is formed of electrically non-conductive or insulating plastic material and has an axially-extending passage through the wall which is separate from the scope-receiving bore. An electrode extends through that passage and is disposed in direct electrical contact with the bearing tube. The electrode wire includes a first section comprising a pair of parallel arms projecting forwardly from the front end of the tube and terminating in a suitable electrode tip which bridges the distal ends of the arms. The electrode also includes a second section in the form of a lead which extends axially from the rear end of the tube. The arms and lead are covered by insulating sleeves which are buried within and bonded to the bearing tube in such a way that extended paths for current flow are provided between those points where the ends of the insulating sleeves terminate within the bearing tube on one hand and the surface of the endoscope stem on the other.

At its proximal or rear end, the electrode lead is provided with an offset portion adapted to establish latching engagement with the spring-loaded connector of the working element. The offset portion thus contributes to an inexpensive and highly effective interconnection between the electrode assembly and working element — an interconnection which insures retention of the electrode assembly by the instrument and which promotes effective electrical contact between the parts.

The method of making the assembly includes the steps of forming a pre-assembled electrode, complete except for the insulation sleeve of the electrode lead and the offset portion at the end of that lead, and inserting the lead into the passage of the bearing tube until the arms of the electrode abut the bearing tube within the enlarged front end of the passage. The insulating sleeve for the lead is then slipped into place, it being noted that an end section of the sleeve is received within a part of the passage of the bearing tube. Thereafter, a suitable liquid potting compound is introduced into portions of the passage at opposite ends of the bearing tube to anchor the parts together and to seal the insulating sleeve of the electrode lead as well as the insulating sleeves of the electrode arms to the bearing tube within opposite ends of the passage. Because of the relative lengths of the electrode lead and the insulating sleeve which is fitted upon it, a tip portion of that lead is exposed and, after the parts are secured together, may be formed to define the offset portion described above.

Other advantages, features, and objects of the invention will become apparent from the specification and drawings.

DRAWINGS

FIG. 1 is a side elevational view, partly fragmentary and in section, of a resectoscope equipped with the new electrode assembly of this invention.

FIG. 2 is an exploded perspective view showing the electrode assembly and its relationship to the sliding block assembly of the instrument's working element.

FIG. 3 is an enlarged longitudinal sectional view of the electrode assembly taken along line 3—3 of FIG. 4.

FIG. 4 is a cross sectional view taken along line 4—4 of FIG. 3.

FIG. 5 is a perspective view of the electrode assembly.

FIGS. 6–8 are perspective views illustrating how the non-conductive bearing tube and the plural section electrode are assembled together.

DETAILED DESCRIPTION

Referring to the drawings, the numeral 10 generally designates a resectoscope comprising four main components, namely, an endoscope 11, a working element 12, a resectoscope sheath 13, and an electrode assembly 14. Endoscope 11 includes an eyepiece 15 and a stem 16, the stem extending through the working element 12 and into the resectoscope sheath 13. A light connection 17 adjacent the proximal end of the rigid endoscope provides means for coupling a light source to the endoscope, such light then being transmitted by means of a fiber bundle (not shown) extending through the stem to the distal end of the endoscope for purposes of illumination. Image transmission from the objective lens at the distal end back to the eyepiece may be achieved by any well known means, such as by a rod lens system or an image-transmitting fiber optic bundle. Since the endoscope construction is well known and may be entirely conventional, further description is believed unnecessary herein.

The working element comprises an instrument body 18 which slidably supports a block assembly 19. The block assembly, which is illustrated in detail in FIG. 2, includes a slide portion 20 provided with a bore 21 through which endoscope guide tube 22 of the body 18 extends (FIG. 1). The block 19 is therefore slidable on the endoscope guide tube 22 between the rearward position depicted in FIG. 1 and a forward position (not shown). A spring 23 urges the block rearwardly into its retracted position. When the instrument is in use, the doctor urges the block forwardly into its extended position by means of thumb ring 24 and then, by reducing the force exerted by his thumb, allows the spring to shift the block rearwardly into its original retracted position.

The endoscope guide tube 22 of the working element 12 projects forwardly from the working element and into the resectoscope sheath 13 as illustrated in FIG. 1. The tube 22, which provides a rigid protective housing for the endoscope stem as well as a guide tube for insertion and removal of the stem, terminates at its distal end 22a a substantial distance short of the distal end 16a of the endoscope. The resectoscope sheath 13, which extends over the endoscope guide tube 22, is provided with a conventional latch mechanism 25 for releasably holding the sheath in the position shown in FIG. 1. By depressing button 25a, the entire collar 25b is shifted downwardly to permit pins 26 to be released from slots 27, such pins projecting laterally from the front end of the body 18 of the working element.

The electrode assembly 14 is shown generally in FIGS. 2 and 5 and in detail in FIGS. 3 and 4. The assembly essentially comprises a non-conductive bearing tube 30 and an electrical conductor or electrode 31 which extends through the wall of the tube and projects beyond opposite ends of that tube. A first section of the electrode takes the form of a pair of spaced parallel arms 32 which angle forwardly and upwardly from the front or distal end of the bearing tube as shown most clearly in FIGS. 2 and 5. At their distal ends, the arms are joined by an electrode tip 33 which is preferably formed of tungsten and which, is in the illustration given, takes the form of a U-shaped cutting loop. It is to be understood that the electrode tip may have other configurations and may be used for coagulating rather than cutting, all being well known in the art. A second section of the electrode takes the form of an electrode lead 34 which extends rearwardly from the proximal end of the bearing tube. The bearing tube has an enlarged bore 35 which slidably receives the distal end portion of endoscope stem 16. In addition, the wall 36 of the bearing tube has a longitudinal passage 37 through which the electrode 31 extends. The wall of the bearing tube provides an uninterrupted separation between passage 37 and bore 35.

In the embodiment illustrated, the electrode 31 is composed of multiple elements as depicted most clearly in FIG. 3. Thus, the arms and cutting loop are formed of a piece of tungsten wire with the arms reinforced by electrically-conductive stabilizing tubes 38. The stabilizing tubes constitute rearward extensions of the arms and receive the front ends of a pair of intermediate wire segments 39. The intermediate segments slope downwardly and inwardly, terminating in rearwardly-projecting lower end portions 39a which are received in the front end of a tubular electrical connector 40. The electrode lead 34 extends into the connector 40 from the rear end thereof as shown in FIG. 3. The stabilizing tubes 38 and the electrical connector 40 are crimped at their ends to maintain all of the electrically-conductive elements of the electrode assembly together as a unit.

It is to be noted that the stabilizing tubes 38 and connector 40 are electrically-conductive components of the complete electrode 31, such components being formed from stainless steel or some other suitable conductive metal. The intermediate segments 39 are shown as elements distinct from arms 32; however, if desired both the arms and the intermediate segments may be formed from the same electrically-conductive metal. In the embodiment shown, the arms and cutting loop are formed of tungsten and although it is desirable to use a metal having the properties of tungsten for the electrode tip 33, such properties are not required for the intermediate conductive segments 39. Hence, the intermediate segments are formed as separate elements from a more readily formable metal (such as copper or a copper alloy) and are then joined to the arms 32 by means of stabilizing tubes 38. The stabilizing tubes therefore perform the dual functions of coupling the parts and rigidifying the spaced arms.

Since the electrical connector 40 extends through passage 37 in engagement with the inner surface of that passage, there is direct electrical contact between that connector and the bearing tube. Direct electrical contact also exists between intermediate segments 39 and the bearing tube (FIGS. 3 and 4). While proximal ends of stabilizing tubes 38 are shown to be spaced slightly from the bearing tube (FIG. 3), in actual practice the parts may be in physical contact because of the practical limits of manufacture and assembly and, in any event, such parts are positioned closely enough to be in arcing relationship. The electrode is therefore in direct electrical contact with the bearing tube; however, it remains insulated from the endoscope stem because the bearing tube is itself formed of insulating or non-conductive plastic material.

Any of a variety of polymeric materials having sufficient rigidity, durability, and dielectric strength may be used to form the bearing tube. With regard to its dielectric properties, the bearing tube must be capable of withstanding a potential difference of at least 5,000 volts between the electrode and the endoscope tube. Particularly effective results have been obtained by forming the bearing tube from an acetal homopolymer marketed under the trade name Delrin by E. I. duPont deNemours & Co., Inc., Wilmington, Delaware, but other suitable plastics are known and may be utilized. Any such material should have a co-efficient of friction (static) on steel no greater than about 0.5, and preferably no greater than 0.3, or, in other words, far lower than the co-efficient of friction of steel on steel. Since plastic materials are softer than the metal (usually stainless steel) of the endoscope stem, there is no danger that the bearing tube 30 will abrade the surface of the stem and, since the entire electrode assembly is intended only for a single use, there is no possibility that any significant wear or dimensional change of the plastic bearing tube will occur before the entire assembly is ready to be discarded. The result is a tube which not only insulates the endoscope from the electrode but also provides a highly effective bearing element for maintaining low resistance to sliding movement of the parts.

Referring to FIG. 3, and also to FIGS. 6 and 7, it will be observed that passage 37 through the plastic bearing tube 14 has an enlarged front or distal portion 37a. The enlargement is generally trough-shaped or V-shaped in cross-sectional configuration, the outer limits being defined by a trough-shaped outer wall portion 41 and the inner limits being defined by the cylindrical outer surface of the inner wall portion 42 (FIGS. 4 and 6). It will also be noted that the enlarged recess or trough-shaped portion 37a of passage 37 is not only open at the front or distal end of the bearing tube but is also partially exposed at opposite sides of that tube by reason of slots or openings 43 (FIG. 6). Such slots do not extend the full axial length of the enlarged recess 37a; as shown most clearly in FIG. 6, the slots terminate at approximately the mid point between the front and rear limits of that recess.

Recess 37a is dimensioned to receive the rear or proximal portions of arms 32 and stabilizing tubes 38, as well as the downwardly converging intermediate segments 39, as best shown in FIGS. 3, 4 and 7. Insulating sleeves 44 extend over nearly the full length of each of the arms, the rear or proximal end 44a of each insulating sleeve terminating at a selected distance in front of the downwardly-converging intermediate segments 39 (FIGS. 4, 5 and 7). The recess 37a, and the lateral slots 43, are dimensioned to receive rear portions of the insulating sheaths 44 when the parts are assembled as shown in FIG. 7. Under such circumstances, the insulating sheaths extend to the rear limits of slots while the electrically-conductive stabilizing tubes 38 and the electrode components to which they are connected continue rearwardly well beyond the limits of thos slots.

The electrode lead 34 which projects rearwardly from the bearing tube 14 is also ensheathed in an insulating sleeve 45 as shown most clearly in FIGS. 2, 3 and 5. Sleeve 45 extends from the rear limits of the electrical connector 40 to a point spaced from the rear or proximal end of electrode lead 34. Specifically, the electrode lead has a tip or proximal end portion 34a exposed so that an effective connection may be made between the electrode and the working element 12. The rear end porton of the electrode lead 34a has an offset section 46 for latching engagement with the connecting means of the working element as described below.

Passage 37 through the bearing sleeve 14 is also provided with an enlarged rear portion 37b as illustrated in FIG. 3. The depth or axial extent of the enlarged rear portion 37b of the passage should be substantial. In the embodiment illustrated, that depth is increased by providing the bearing tube with a rearwardly projecting collar extension 14a; however, it is believed apparent that somewhat similar results might be achieved by eliminating the collar extension and increasing the depth of the enlarged portion 37b of the passage, or by extending the full cross-sectional dimension of the bearing sleeve to the rear limits of collar 14a. In any case, the substantial axial extent of space 37b plays an important part in preventing arcing in the final assembly because it provides an extended electrical path between the uninsulated portion of the electrode disposed within (and in direct electrical contact with) the bearing tube and the metal stem of the endoscope 16.

Similarly, the axial depth of slots 43 at the distal end of the bearing tube, and the fact that the proximal ends 44a of the insulating sleeves of arms 32 are disposed at the rear limits of those slots, contribute significantly in preventing arcing between the endoscope tube and the uninsulated portion or portions of the electrode disposed within passage 37 of the bearing tube.

The diameter of the cylindrical enlargement 37b at the proximal end of the bearing tube is substantially greater than the outside diameter of insulating sleeve 45. As a result, an annular space is formed between the outside surface of the insulating sleeve 45 and the inside surface of the enlargement 37b. That space is filled with an insulating plastic resin during the final stage of fabricating the electrode assembly. Similarly, the recess or enlarged portion 37a of the passage 37 at the front or distal end of the bearing tube is filled with an insulating and sealing plastic material during the final stages of fabrication. The plastic potting material is not shown in FIG. 3 (either at the front or the rear ends of the bearing tube) for clarity of illustration; however, the potting material 47 is depicted in FIG. 8. It will be observed that such material fills the entire recess 37a (and also the space 37b at the rear of the bearing tube) and that such material seals the rear portions of the insulating sleeves 44 to the bearing tube to block the flow of fluids into passage 37a and into contact with the uninsulated portion of the electrode disposed within that passage. While any suitable potting material may be used, one which is non-conductive and which bonds securely to the material of the bearing tube, particularly effective results have been achieved with plastic resins such as epoxy compounds.

In assembling the electrode 31 to the bearing tube 30, the electrode is first preassembled to a condition similar to that shown in solid lines in FIG. 5 except that (1) insulating sleeve 45 is omitted and (2) the offset 46 is not formed in the end portion 34a of the electrode lead. The straight undeformed and uninsulated electrode lead is inserted rearwardly into the enlarged front portion 37a of passage 37 until no further rearward movement is possible. At that time, the parts will assume the relationship depicted in FIG. 7. Thereafter, insulating sleeve 45 is slipped over the straight electrode lead (FIG. 8) until the front end of that sleeve is received within the enlarged portion 37b of passage 37. The potting material is then injected into the enlarged front portion 37a and enlarged rear portion 37b of the passage to fill those cavities and seal them against fluid ingress in the manner already described. Finally, in the last stage of fabrication, the exposed rear end 34a of the electrode is formed to provide the offset 46.

Referring to FIGS. 1 and 2, the exposed rear portion 34a of the electrode lead is received within bore 50 formed in the slidable block 19 of the working element 12. That bore is generally parallel with the main bore 21 through which the endoscope guide tube 22 of the body 18 extends although, as shown in FIG. 1, bore 50 may be inclined slightly with respect to bore 21 if so desired. A plunger 51 is mounted for reciprocatory movement in a bore 52 which intersects bore 50. A compression spring urges the plunger downwardly into the lowered position shown in FIG. 1 but the force of that spring may be overcome, and the plunger may be shifted into a raised position, by upward pressure on the exposed knob portion 54 of that plunger. The plunger is retained by the slidable block by means of a collar 55 which is threadedly connected to the block and through which the plunger extends.

When the plunger is shifted upwardly into its raised position, an opening 56 in that plunger is shifted into alignment with bore 50. Opening 56 is large enough to receive the end portion 34a of the electrode lead despite the offset 46 formed in that portion. Furthermore, the depth of bore 50 is such that when the electrode lead is inserted as far as it will go into the bore, the offset portion is vertically aligned with plunger bore 52. Hence, to latch the electrode as illustrated in FIG. 1, a user simply inserts the end portion 34a of the electrode lead into bore 50 while button 54 is held in a raised position. Upon release of the button, spring 53 will then urge the plunger downwardly to secure the electrode in the latched position depicted in FIG. 1. In that position, the plunger firmly engages the downwardly offset portion 46 of the electrode and, because of such offset, effectively holds the electrode lead against rotation and against axial displacement. To release the electrode, button 54 is simply urged upwardly to bring opening 56 into alignment with bore 50, and the electrode is then pulled forwardly away from the working element.

The plunger 51 is formed in sections so that button 54 may be of insulating material while the upper section 51a (to which the button is secured by threaded stub 51b) may be formed of electrically-conductive material. As shown in FIG. 2, the upper section 51a is provided with surface slidably engaged by electrical contact or brush 57, the brush being held in sliding engagement with the plunger by means of spring 58. A tubular conductor 59 defines a socket 60 for receiving the plug of a suitable electrical lead (not shown) and an insulating tube 61 is threadedly secured to the slidable body and retains the conductor 59 in proper position.

While in the foregoing an embodiment of the invention has been disclosed in considerable detail for purposes of illustration, it will be understood by those skilled in the art that many of these details may be varied without departing from the spirit and scope of the invention.

We claim:

1. A cutting electrode assembly for use with a rigid endoscope-equipped urological instrument, comprising a bearing tube having a wall defining an axial bore for slidably receiving the metal stem of a rigid endoscope, said tube being formed of electrically insulating polymeric material and having an axially-extending passage through said wall separated from said bore, and electrode means extending through said passage and disposed in direct electrical contact with said bearing tube, said electrode means having a first end portion extending beyond one end of said tube and a second end portion projecting beyond the tube's opposite end, said first end portion comprising a pair of parallel arms terminating in and connected by an electrode tip, said second end portion including means for connecting said electrode means to a source of electrical current.

2. The assembly of claim 1 in which said arms are ensheathed in insulating sleeves, said sleeves extending into said passage and being sealed in fluid-tight relation to said tube.

3. The assembly of claim 2 in which said sleeves are formed of polymeric material and are sealed to said tube by a non-conductive potting compound.

4. The assembly of claim 2 in which said wall includes a pair of lateral slots on opposite sides of said tube at said one end of said tube, said sleeves extending into said passage adjacent said slots and being laterally exposed through said slots.

5. The assembly of claim 1 in which said second end portion of said electrode means comprises a substantially straight electrode lead, and an electrically-insulating sleeve extending about a major portion of the length of said lead.

6. The assembly of claim 5 in which said electrode lead includes an end portion extending into said passage of said tube, said sleeve having an end portion extending about said end portion of said lead and being disposed within said passage, and non-conductive sealing means bonding said end portion of said sleeve to said tube within said passage.

7. The assembly of claim 5 in which said connecting means comprises a free end portion of said lead remote from said tube and extending beyond said insulating sleeve, said free end portion including latching means for attachment to and retention by a urological instrument, said latching means comprising an offset zone formed in said free end portion.

8. The assembly of claim 1 in which said polymeric material of said bearing tube has a co-efficient of friction on steel no greater than 0.5.

9. The assembly of claim 8 in which said polymeric material of said bearing tube has a co-efficient of friction on steel no greater than about 0.3.

10. A method of making the electrode assembly of claim 1 comprising the steps of inserting said second end portion of said electrode means into said passage at said one end of said bearing tube and then sliding said bearing tube along said electrode means until said arms of said electrode means abut said one end of said bearing tube within said passage, then sliding an insulating sleeve onto said second end portion of said electrode means until a section of said sleeve is received within said passage at said opposite end of said tube, then introducing a hardenable liquid into said passage at both ends of said bearing tube to anchor the parts together and to seal said insulating sleeve to said bearing tube within said passage.

11. The method of claim 10 in which said arms are ensheathed in insulating sleeves which extend into said passage at said one end of said bearing tube at the completion of said inserting step, said step of introducing a hardenable liquid being effective to seal said insulating sleeves of said arms to said bearing tube within said passage.

12. The method of claim 10 in which a terminal section of said second end portion of said electrode means is exposed beyond said insulating sleeve following said inserting step, and in which there is the further step of forming an offset in said terminal section of said second end portion of said electrode means.

13. A cutting electrode assembly for use with a rigid endoscope-equipped urological instrument, comprising a bearing tube having a wall defining an axial bore for slidably receiving the stem of a rigid endoscope, said tube being formed of electrically non-conductive plastic material and having an axially-extending passage through said wall separated from said bore, and an electrode extending through said passage and disposed in direct electrical contact with said bearing tube within said passage, said electrode having a first end portion extending beyond one end of said tube and a second end portion projecting beyond the tube's opposite end, said first end portion comprising a pair of parallel arms having distal ends joined by an electrode tip, said tube having a pair of slots formed in said wall at said one end thereof, said arms being ensheathed in a pair of electrically-insulating sleeves extending into said pair of slots, and non-conductive sealing means bonding and sealing said sleeves to said tube within said slots, said second end portion of said electrode including connecting means for connecting said electrode to a source of electrical current.

14. The assembly of claim 13 in which said slots directly communicate with a portion of said passage adjacent said one end of said tube, said sealing means also being disposed within said portion of said passage communicating with said slots.

15. The assembly of claim 13 in which said second end portion of said electrode comprises a substantially straight electrode lead, and an electrically-insulating sleeve extending about a major portion of the length of said lead.

16. The assembly of claim 15 in which said electrode lead includes an end portion extending into said passage of said tube, said sleeve having an end portion extending about said end portion of said lead and being disposed within said passage, and non-conductive sealing means bonding said end portion of said sleeve to said tube within said passage.

17. The assembly of claim 15 in which said connecting means comprises a free end portion of said lead remote from said tube and extending beyond said insulating sleeve, said free end portion including latching means for attachment to and retention by a urological instrument, said latching means comprising an offset zone formed in said free end portion.

18. The assembly of claim 13 in which said non-conductive plastic material of said bearing tube has a coefficient of friction on steel no greater than about 0.5.

19. The assembly of claim 18 in which said co-efficient of friction is no greater than about 0.3.

* * * * *